United States Patent
Segawa et al.

(10) Patent No.: US 10,219,844 B2
(45) Date of Patent: Mar. 5, 2019

(54) SPINE FIXATION DEVICE AND SPINE FIXATION SYSTEM

(71) Applicant: Robert Reid, Inc.

(72) Inventors: Tsuyoshi Segawa, Suginami-ku Tokyo (JP); Carl Michael Nilsson, Moreland Hills, OH (US)

(73) Assignee: ROBERT REID, INC. (JP)

( * ) Notice: Subject to any disclaimer, the term of this patent is extended or adjusted under 35 U.S.C. 154(b) by 87 days.

(21) Appl. No.: 14/668,019

(22) Filed: Mar. 25, 2015

(65) Prior Publication Data

US 2016/0278832 A1 Sep. 29, 2016

(51) Int. Cl.
*A61B 17/70* (2006.01)

(52) U.S. Cl.
CPC ...... *A61B 17/7074* (2013.01); *A61B 17/7037* (2013.01)

(58) Field of Classification Search
CPC .................................. A61B 17/70–17/7092
See application file for complete search history.

(56) References Cited

U.S. PATENT DOCUMENTS

| | | | | |
|---|---|---|---|---|
| 8,361,122 B2* | 1/2013 | Barrus | ............... | A61B 17/7032 606/267 |
| 8,888,827 B2* | 11/2014 | Harper | ............... | A61B 17/7056 606/266 |
| 9,358,047 B2* | 6/2016 | Mishra | ............... | A61B 17/7037 |
| 2004/0138662 A1* | 7/2004 | Landry | ............... | A61B 17/1604 606/86 A |
| 2010/0152787 A1* | 6/2010 | Walsh | ............... | A61B 17/7037 606/308 |
| 2010/0198272 A1* | 8/2010 | Keyer | ............... | A61B 17/7082 606/302 |
| 2010/0234902 A1* | 9/2010 | Biedermann | ...... | A61B 17/7032 606/305 |
| 2011/0152949 A1* | 6/2011 | Biedermann | ...... | A61B 17/7037 606/305 |
| 2013/0338721 A1* | 12/2013 | Biedermann | ...... | A61B 17/7037 606/305 |

* cited by examiner

*Primary Examiner* — Nicholas Plionis
*Assistant Examiner* — Steven Cotroneo
(74) *Attorney, Agent, or Firm* — Tarolli, Sundheim, Covell & Tummino LLP (57) ABSTRACT

A spine fixation device including an elongated bone screw partially embedded in a vertebra of a spine and a retaining head that can receive a rod and a head of the bone screw. The retaining head has an inner member that includes a screw head receiving section for receiving the screw head. The retaining head further has an outer member that includes an inner face that can contact an outer face of the screw head receiving section. When the inner face is in contact with the outer face, the screw head receiving section applies pressure to the screw head to fixate the relative angle between the bone screw and the retaining head.

11 Claims, 10 Drawing Sheets

SPINE FIXATION DEVICE AND SPINE FIXATION SYSTEM

TECHNICAL FIELD

The invention is directed to a spine fixation device for fixating a spine and a spine fixation system.

BACKGROUND

Currently, surgical procedures for cervical, lumbar, etc. spine fixation, correction, stabilization, etc. involve attaching and fixating a rod to a spine fixation device secured to a vertebral body. An appropriate rod is arranged at a predetermined position along the spine according to a known technique.

Different known spine fixation devices can be used depending on the patient's spinal disease or the type of surgery. One known spine fixation device includes a retaining head configured to hold a rod and a bone screw that screws into a vertebra as one unit. The known spine fixation device has features that can prevent relative rotation between the retaining head and the bone screw. The retaining head and the bone screw are manufactured separately, and have a rotating/revolving feature that allows free relative rotation between the retaining head and the bone screw.

The known spine fixation device has a pressure element arranged inside the retaining head for the head of the bone screw and a place for insertion of the rod. The pressure element pushes the head of the bone screw against a head part as is known in the art to hold and prevent rotation of the bone screw (for example, see Japanese Patent Application No. 2011-206538). However, this construction puts the bone screw in a condition where it is temporarily fixated within the retaining head. For example, during surgery to fix a deformed spine of a scoliosis patient, when there is a heavy load against the retaining head and the bone screw, the relative angle between the retaining head and the bone screw can change. To prevent changing of the angle, a ring can be included that exerts pressure on the bone screw head due to the pressure element within the holder part, thereby fixing the relative angle between the bone screw and the retaining head.

In the above known spine fixation device, the ring that improves the push pressure on the head of the bone screw is manufactured separately from a set screw responsible for fixing the rod. Because of this, the number of parts of the spine fixation device increases, which complicates the configuration of the spine fixation device and also causes an increase in size. Furthermore, the ring and the set screw each require an exclusive tool to fasten each part. As a result, there is an increase in cost to have the appropriate equipment.

The present invention is designed with these problems in mind, so that the object of the present invention is to supply a spine fixation device and a spine fixation system that can readily fix a bone screw and a retaining head.

SUMMARY

In order to solve the above problem, the spine fixation device of the present invention includes a rod for fixating a spine and an elongated bone screw partially embedded in a vertebra of the spine. A retaining head holds the rod and the bone screw. The retaining head includes an inner member having a head receiving section for receiving a screw head of the elongated bone screw and an outer member surrounding the inner member. The inner member has an outer face that contacts an inner face of the outer member. Contact between the outer face and the inner face results in pressure being applied to the screw head to fix the elongated bone screw at an angle relative to the retaining head.

The inner face and the outer face gradually decrease in diameter along a Z-axis. The inner member moves along the Z-axis to put the inner face in contact with the outer face.

The inner member is divided in the circumferential direction about the Z-axis into parts. The inner member moves along the Z-axis such that the inner face squeezes the inner member to cause the parts of the inner member to narrow such that pressure is applied to the screw head.

The inner member has a rod receiving section for receiving the rod. The rod is moved along the Z-axis to cause movement of the inner member along the Z-axis to put the inner face in contact with the outer face.

The outer member has a set screw receiving section for receiving a set screw. The set screw is rotated to fixate the rod in the rod receiving section. The set screw is configured to apply pressure to the rod in a direction along the Z-axis.

The relative angle between the elongated bone screw and the retaining head can be maintained when the set screw is removed.

The retaining head can be detached from the screw head when the bone screw is not fixed at the angle relative to the retaining head.

The spine fixation device may be part of a spine fixation system that includes an unlocking device. The unlocking device unlocks the angle that is fixed between the bone screw and the retaining head. The unlocking device has a positioning member and a screw. The positioning member positions the unlocking device relative to the outer member. The screw is received by an unlocking female screw provided on the inner member to allow the inner member to be moved relative to the outer member along the Z-axis such that the outer face is moved out of contact with the inner face.

With the present invention, it is possible to fixate the relative angle between the bone screw and the retaining heed in a much more simple way.

Furthermore, an instrument is shown, which can be used to quickly release the fixed angle between bone screw and retaining bead. In addition, the same instrument can also be used to remove the retaining head off of the bone screw.

Below is an explanation of the present invention with reference being made to the figures. However, it is understood that the invention's scope is not limited to the examples illustrated in the figures.

DETAILED DESCRIPTION

Figure 1:
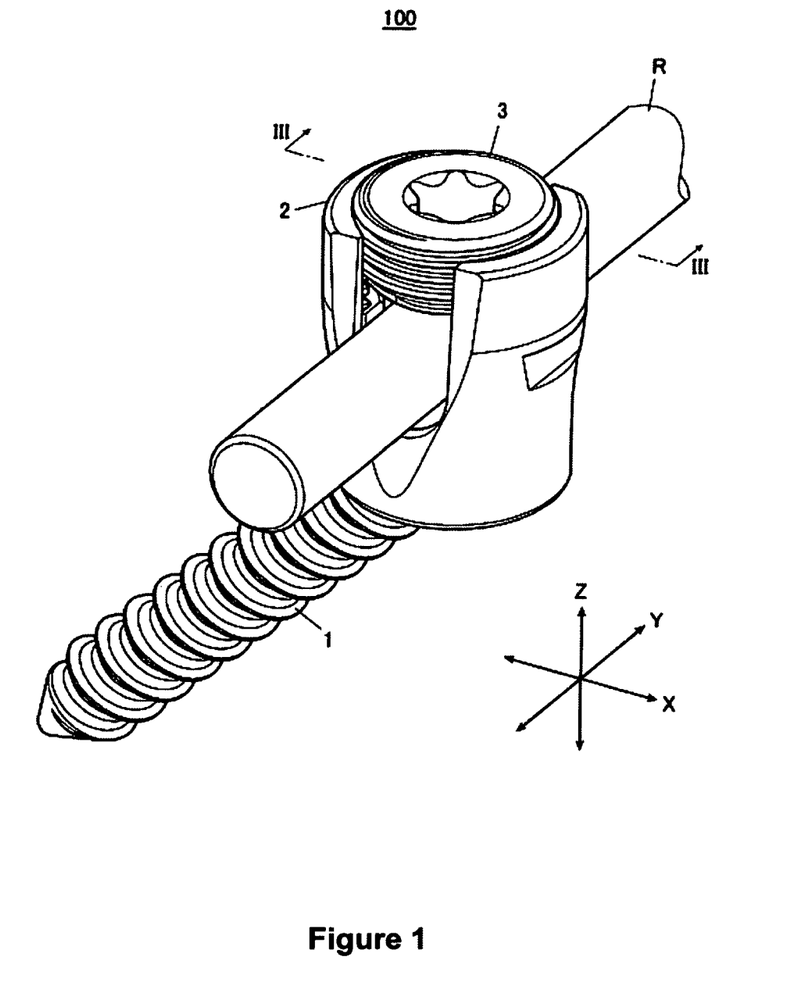
FIG. 1 is an isometric view of one embodiment of the spine fixation device of the present invention.
Figure 2:
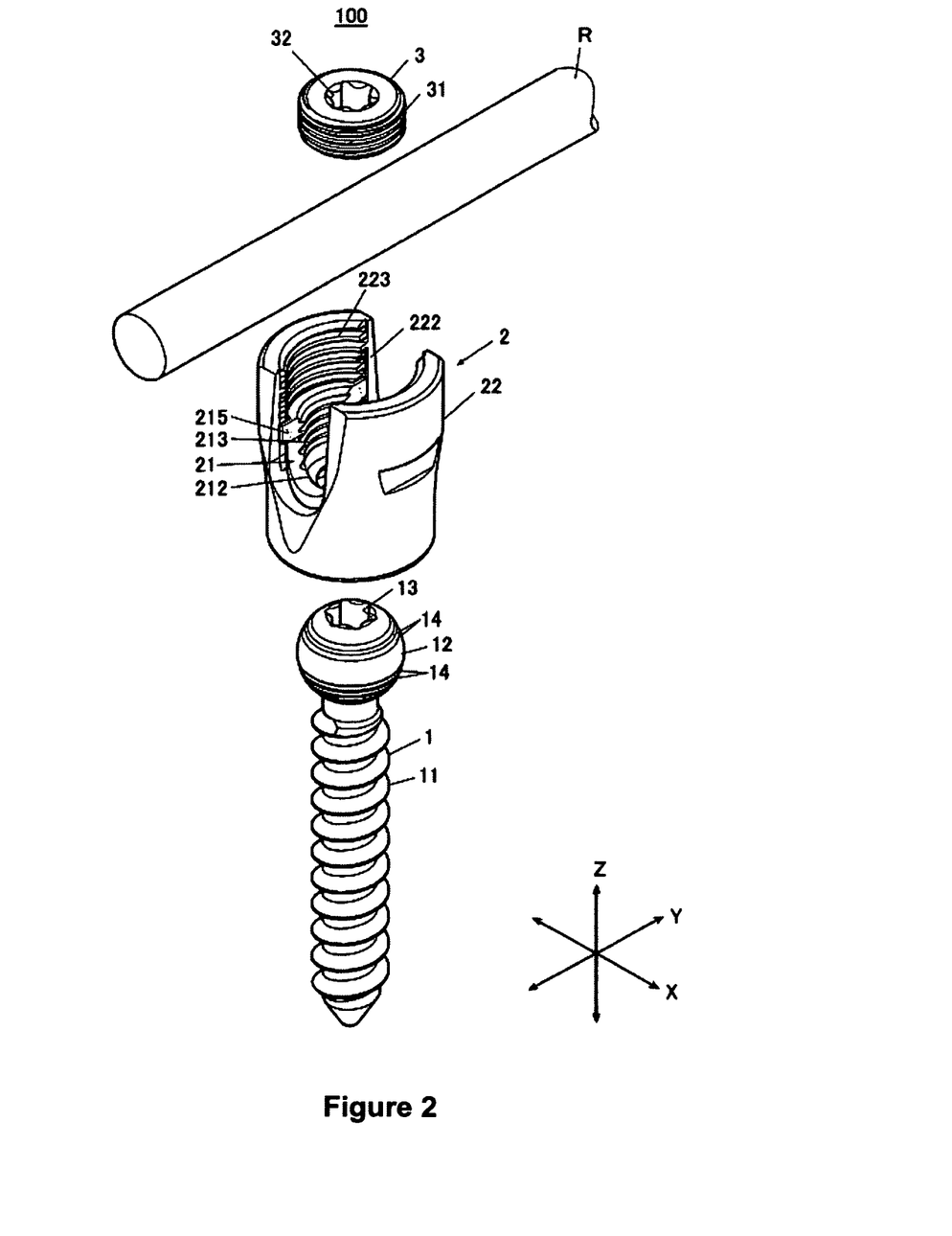
FIG. 2 is an exploded view of the spine fixation device in FIG. 1.
Figure 3:
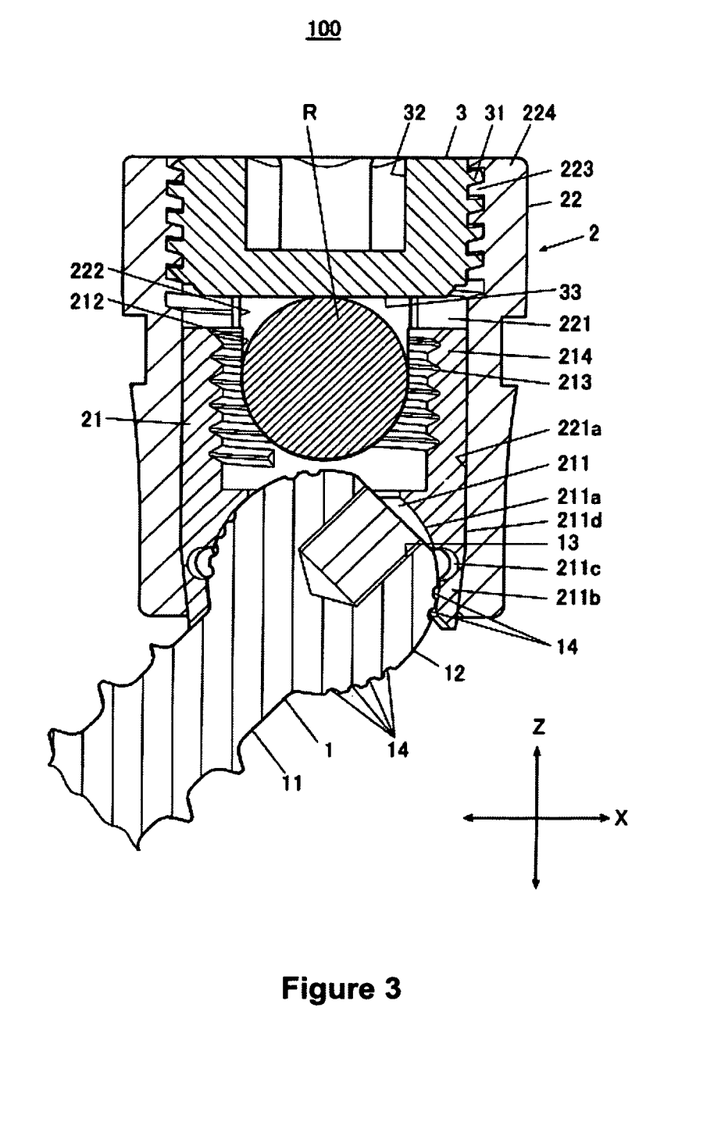
FIG. 3 is a cross section view of the spine fixation device in FIG. 1 through III-III.

FIG. 1 is an isometric view of one preferred embodiment of a spine fixation device 100. FIG. 2 is an exploded isometric view of the spine fixation device 100, and FIG. 3 is a cross section view of the spine fixation device through III-III in the explanation below, the spine fixation device 100 is installed on vertebrae B of a spine V (see FIG. 8). The spine V extends along a Y-axis, an X-axis extends horizontally and orthogonal relative to the Y-axis, and a Z-axis extends vertically and orthogonal relative to the Y-axis.

The spine fixation device 100 can, for example, adjust and/or stabilize the vertebrae B of the spine V that extend along the Y-axis by placing two cylindrical rods R along the spine V. Specifically, as shown in FIGS. 1-3, the spine fixation device 100 can include a bone screw 1 that is screwed into a vertebra B, a retaining head 2 that is fixed to the bone screw 1, a rod R that extends through the retaining head 2, and a set screw 3 that secures the rod R to the retaining head 2.

A portion of the bone screw 1 is embedded into the vertebra B. Specifically, the bone screw 1 has a screw body 11 that is elongate along the Z-axis and is adapted to be screwed into the vertebra B. One end of the screw body 11 includes a screw head 12 that is not embedded into the vertebra B.

The screw head 12 is substantially spherically shaped and includes a tool receiving depression 13. The tool receiving depression 13 is adapted to receive a tool for rotating the bone screw 1 to insert the bone screw 1 into the vertebra B.

Depressions 14 are provided on an outside face of the screw head 12. The depressions 14 (or grooves) extend around a central axis of the bone screw 1, but can also be arranged in other or multiple directions. The depressions 14 are located on the outside face of the screw head that is adjacent the screw body 11 and also on the outside face of the screw head that is adjacent the tool receiving depression 13. The location of the depressions 14 decrease contact surface area between a curved surface 211a of a screw head receiving section 211 (discussed below) and the screw head 12 and, thereby, increase surface contact pressure for increased rotational stability.

The retaining head 2 is configured to retain the bone screw 1 and the rod 2. Specifically, the retaining head 2 has an inner member 21 (see FIG. 4a) where the screw head 12 is placed and an outer member 22 (see FIG. 5a) that surrounds the inner member 21.

Figure 4A:
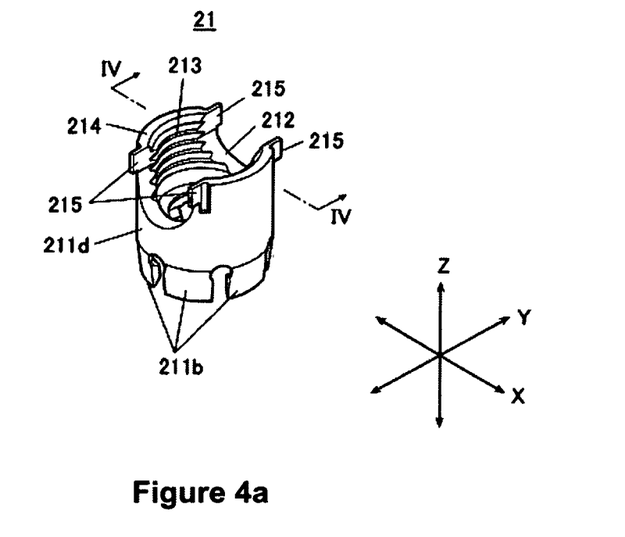
FIGS. 4a and 4b are views of an inner member of the retaining head comprising the spine fixation device in FIG. 1.
Figure 4B:
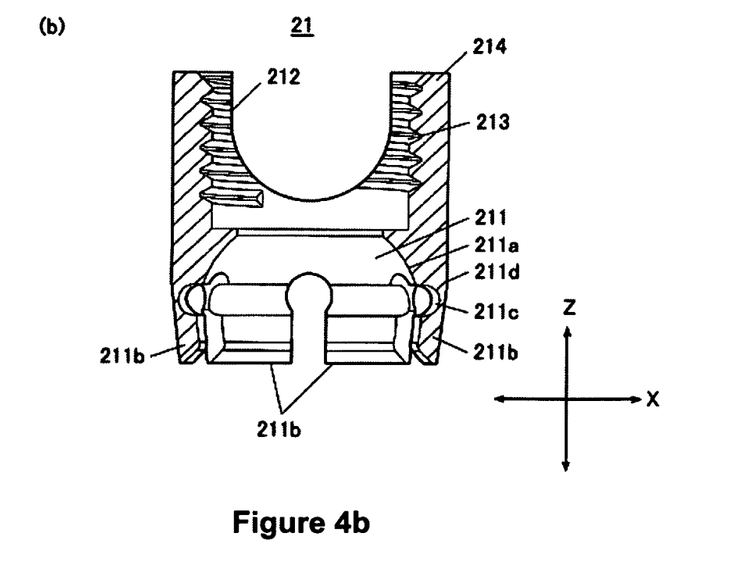

FIG. 4a is an isometric view of the inner member 21 of the retaining head 2. FIG. 4b is a cross section view of the inner member 21 through IV-IV. As shown in FIGS. 4a and 4b, the inner member 21 is, for example, cylindrically shaped and includes a screw head receiving section 211 for receiving the screw head 12 of the bone screw 1. The inner member 21 further includes an inner rod receiving section 212 for receiving the rod R and an unlocking female screw 213 for receiving a screw 201a of an unlocking device 200 (discussed below).

The screw head receiving section 211 is open toward the vertebrae B when the inner member 21 of the spine fixation device 100 is attached to the screw head 12. The screw head receiving section 211 includes a curved surface 211a that is constructed to have roughly the same arc and radius of the screw head 12 of the bone screw 1. The screw head receiving section 211 further includes a plurality of arms 211b that extend toward the vertebrae B beyond the curved surface 211a.

The arms 211b are defined by a plurality of cuts that are spaced equidistant from one another and extend into the screw head receiving section 211 along the Z-axis such that the arms 211b are spaced equally around the Z-axis. Additionally, an inner face of the arms 211b are constructed to have the same arc and radius of the screw head 12.

A reduced thickness part 211c is provided in an area between the arms 211b and the curved surface 211a. The reduced thickness part 211c is thinner in the direction of the X-axis and Y-axis when compared to the arms 211b and the curved surface 211a. Specifically, the reduced thickness part 211c extends into the screw head receiving section 211 in a direction along the X-axis and the Y-axis at the boundary between the arms 211b and the curved surface 211a. The reduced thickness part 211c can also extend in the opposite (outward) direction.

Furthermore, when the arms 211b are not deformed, the inside arc of the arms 211b is structured to have a smaller radius than the radius of the outside arc of the screw head 12. On the other hand, the arms 211b can be deformed elastically in a direction along the X-axis and the Y-axis such that the radius of the inside arc of the arms 211b is roughly the same as, or larger than, the radius of the outside arc of the screw head 12. The screw head 12 can be forced into the arms 211b to spread the arms 211b in a direction along the X-axis and the Y-axis to enable placement of the screw head 12 inside the screw head receiving section 211. In this condition, the bone screw 1 is located such that the screw head 12 is closer toward the curved surface 211a rather than the arms 211b. The arms 211b can elastically recover their original position and enclose the screw head 12. Specifically, the arms 211b are inwardly biased in a direction along the X-axis and the Y-axis to temporarily prevent the screw head 12 from separating from the screw head receiving section 211.

As explained above, the bone screw 1 is configured to be removable from the screw bead receiving section 211 when the bone screw 1 is not fixed at an angle relative to the retaining head 2. The process by which the bone screw 1 is fixed at an angle relative to the retaining head 2 will be discussed later.

The arms 211b of the screw head receiving section 211 include an outer face 211d that is shaped to slope diagonally inward relative to an edge of the receiving section 211. In essence, in comparison to an inner face of the arms 211b, the outer face 211d is tapered with a diameter that gradually reduces along the Z-axis.

The inner rod receiving section 212 is provided on the inner member 21 opposite the screw head receiving section 211. The inner rod receiving section 212 is defined by cuts of a specific depth into the inner member 21 in a direction along the Z-axis. Specifically, the inner rod receiving section 212 is provided on the inner member 21 for receiving the rod R and includes two sidewalls 214 (see FIG. 4) that define a U-shaped structure. The space between the sidewalls 214 in a direction along the X-axis is roughly the same as, or slightly larger than, the diameter of the rod R. In addition, the inner rod receiving section 212 is curved and resembles a half-circle having a diameter equal to the diameter of the rod R such that the inner rod receiving section 212 contacts the rod R about the circumference of the rod R.

A plurality of plank shaped parts 215 are provided on an edge of the inner rod receiving section 212. The planked shaped parts 215 prevent the inner member 21 from rotating relative to the outer member 22.

The unlocking female screw 213 is provided on the sidewalls 214 and extends toward the X-axis and Y-axis. Specifically, the unlocking female screw 213 includes threads having a specified pitch and depth extending toward the X-axis and Y-axis on the inner face of the sidewalls 214. When using the unlocking device 200 (discussed below) to unlock a fixed relative angle between the bone screw 1 and the retaining head 2, the unlocking female screw 213 is configured to receive an unlocking male screw 201a provided on a screw member 201 of the unlocking device 200.

Figure 5A:
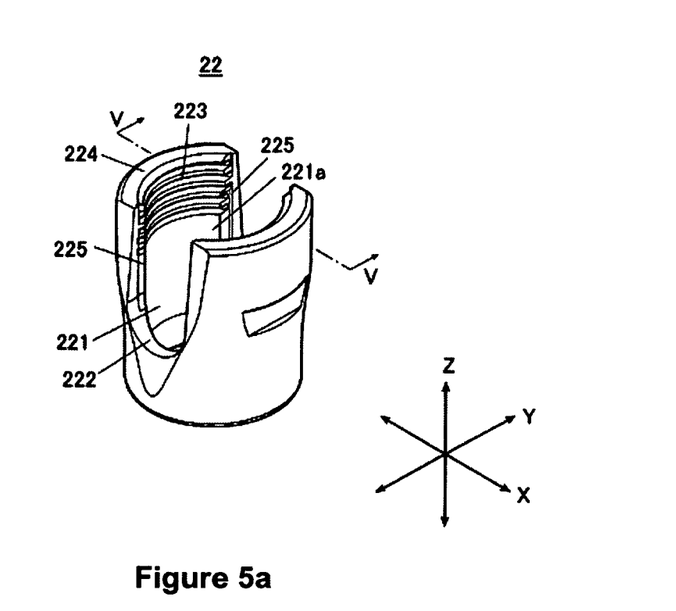
FIGS. 5a and 5b are views of an outer member of the retaining head comprising the spine fixation device in FIG. 1.
Figure 5B:
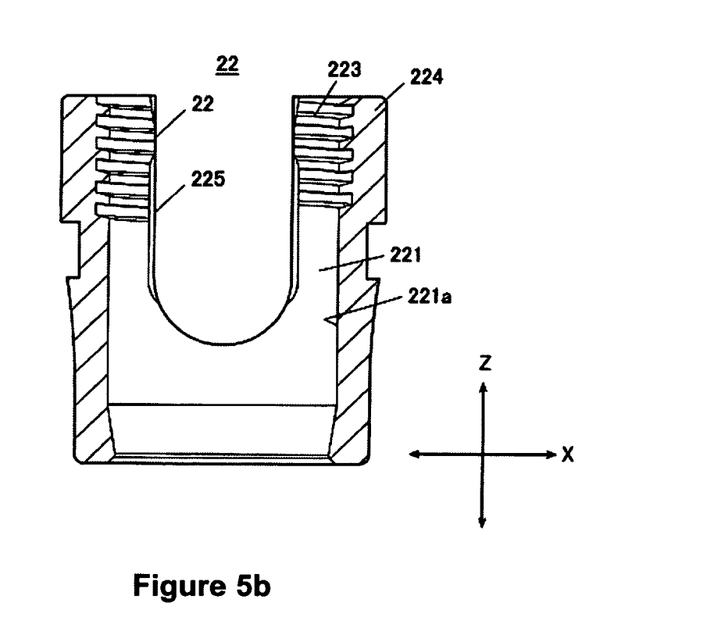

FIG. 5a is an isometric view showing the outer member 22 of the retaining head 2. FIG. 5b is a cross section of the outer member 22 taken through V-V of FIG. 5a. As shown in FIGS. 5a and 5b, the outer member 22 has a substantially cylindrical shape and has a storage part 221 configured to receive the inner member 21. The outer member 22 also includes an outer rod receiving section 222 for receiving the rod R and a set screw receiving section 223 for receiving the set screw 3.

The storage part 221 has an inner face 221a that has roughly the same shape as the outer face of the inner member 21. Specifically, the inner face 221a is shaped similarly to the arms 211b of the inner member 21. In essence, the storage part 221 and the inner face 221a have portions that are partially tapered with a diameter that gradually decreases along the Z-axis. In addition, the portions of the inner face 211a that are not tapered are structured so that the arc and radius of the inner face 211a is the same as the arc and radius of the cylindrical part of the inner member 21.

In addition, the length of the inner face 221a along the Z-axis is longer than the length of the inner member 21 along the Z-axis. Furthermore, the tapered part of the inner face 221a has an arc and radius that is the same as, or slightly larger than, the arc and radius of the arms 211b of the inner member 21. The portion of the inner face 221a that is non-tapered has an arc and radios that is roughly the same as or slightly larger than, the arc and radius of the non-tapered portion of the inner member 21. Due to this, when the inner member 21 is located in the storage part 221, the inner member 21 is able to move in a direction along the Z-axis relative to the outer member 22 while the outer face of the inner member 21 is in contact with the inner face 221a of the storage part 221. In essence, the inner face 221a of the storage part 221 and the outer face 211d of the screw head receiving section 211 are in contact with one another.

The outer rod receiving section 222 is defined by cuts of a specific depth into the outer member 22 along the Z-axis. Specifically, the outer rod receiving section 222 is configured to receive the rod R and has sidewalls 224 that have U-shape cutouts (see FIG. 5b). In addition, the space between the sidewalls 224 in a direction along the X-axis is roughly the same as, or slightly larger than, the diameter of the rod R. In addition, an edge of the outer rod receiving section 222 is curved and roughly formed as a half circle with roughly the same radius as the rod R and is in contact with the circumference of the rod R.

The set screw receiving section 223 extends into the sidewalls 224 of the outer member 22 in a direction along the X-axis and Y-axis. Specifically, the set screw receiving section 223 is structured continuously along an edge of the storage part 221 that includes the sidewalls 224. The set screw receiving section 223 is defined by threads of a specified pitch and depth that extend into an inner face of the sidewalls 224 in a direction along the X-axis and Y-axis. The set screw receiving section 223 is configured to interact with a male screw section 31 (discussed below) provided on the circumference of the set screw 3.

Figure 6A:
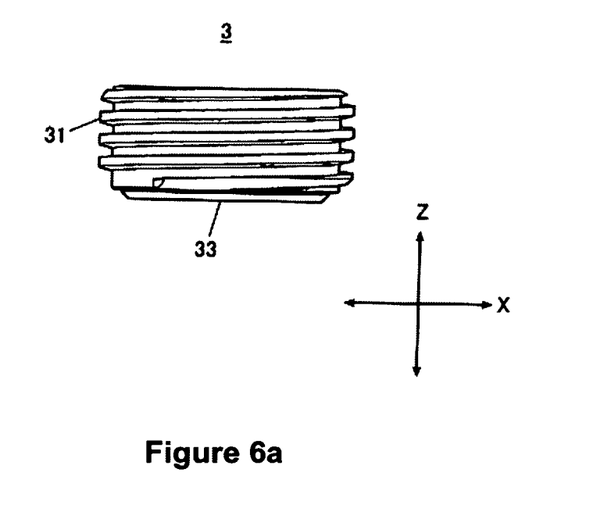
FIGS. 6a and 6b are views of the set screw comprising the spine fixation device in FIG. 1.
Figure 6B:
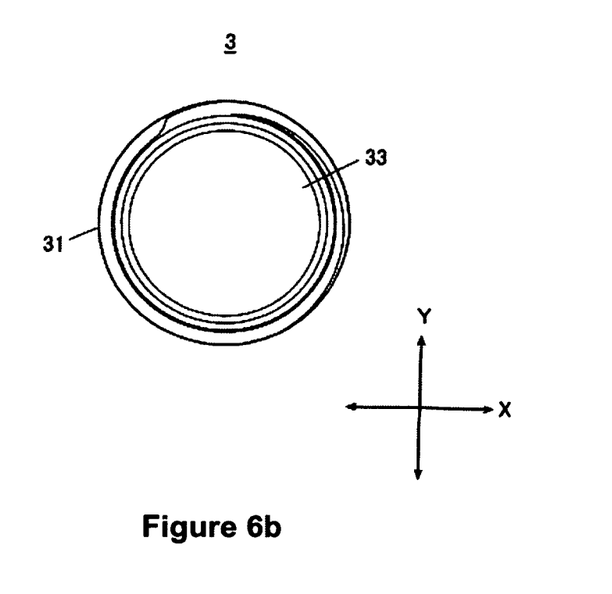

FIG. 6A is a side view of the set screw 3. FIG. 6b is a bottom view of the set screw 3. As shown in FIGS. 6a and 6b, the set screw 3 has a male screw section 31 along the circumference of the set screw 3. The male screw section 31 is configured to thread into the set screw receiving section 223 of the outer member 22.

The male screw section 31 has a specified pitch thread, and can be screwed into the threads of the set screw receiving section 223. In addition, at the beginning of the threading, the male screw section 31 has a recessed cut (see FIG. 6b) in a circumferential direction centered along an axis extending toward the Z-axis. The cut facilitates the engagement of the male screw section 31 with the set screw receiving section 223.

In addition, on one end of the set screw 3 there is provided a tool receiving depression 32 (see FIG. 3) configured to facilitate rotation of the sat screw 3.

In use, the rod R is placed in the outer rod receiving section 223 and the inner rod receiving section 222. The set screw 3 is screwed into the set screw receiving section 223 of the outer member 22 to move the rod R in a direction along the Z axis to fix the rod R. A tool is inserted into the tool receiving depression 32 to screw the male screw section 31 into the set screw receiving section 223 by rotating the set screw 3 about the Z-axis to move the set screw 3 in a direction along the Z-axis. Then, a planar part 33 of the fixing screw 3 will come into contact with a side circumference of the rod R to move the rod R toward the vertebrae B and the inner rod receiving section 212, as well as the outer rod receiving section 222, to fixate the rod R to the retaining head 2.

At this time, when the rod R is moved toward the vertebrae B in a direction along the Z-axis, the inner member 21 moves toward the vertebrae in a direction along the Z-axis relative to the outer member 22. The curved surface 221a of the storage part 221 of the outer member 22 comes into contact with the outer face 211d of the arms 211b of the screw head receiving section 211 such that inner face of the screw head receiving section 211 applies pressure to the screw head 12 of the bone screw 1. In this condition, when the rod R is moved toward the vertebrae B in a direction along the Z-axis due to the set screw 3, the rod R contacts the inner rod receiving section 212 to move the inner member 21 relative to the outer member 22 toward the vertebrae B in a direction along the Z-axis. The outer circumference of the rod R is pressured when the set screw 3 touches an inner edge of the outer rod receiving section 222 such that relative movement of the inner member 21 and the outer member 22 is stopped.

Moreover, by having the inner member 21 move toward the vertebrae B in a direction along the Z-axis relative to the outer member 22, the arms 211b of the screw head receiving section 211 are forced into a portion of the storage part 221 that has an inner diameter that is smaller than the outer diameter of the arms 211b. Due to this, the inner face 221a of the storage part 221 presses against the outer face 211d of the screw head receiving section 211 so as to narrow the spaces between the arms 211b such that the curved surface 211a and the inner face of the arms 211b press toward the screw head 12 of the bone screw 1. Specifically, by narrowing the spaces between the arms 211b pressure is applied to the screw head 12 of the bone screw 1 by the arms 211b. Moreover, the screw head 12 is pressured by the arms 211b in a direction opposite to the movement of the inner member 21 such that the screw head 12 is pushed against curved surface 211a (see FIG. 7b). Due to this, when the curved outer surface of the screw head 12 is in contact with the curved surface 211a, the depressions 14 of the screw head 12 are locked into the arms 211b.

By this way, when the inner face 221a of the of the outer member 22 and the outer face 211d of the screw head receiving section 211 are in contact, the screw head 12 of the bone screw 1 is pressured by the screw head receiving section 211, and the angle of the bone screw 1 relative to the retaining head 2 is fixated. In this condition, even if the set screw 3 is released from the set screw receiving section 223, the angle of the bone screw 1 relative to the retaining head 2 can still be maintained in the fixated condition (see FIG. 7c).

Each part of the aforementioned spine fixation device, including the bone screw 1, the retaining head 2, and the set screw 3 are, for example, manufactured out of titanium having specified material properties, or with alloys and/or stainless material used in the medical field.

A method for fixating a spine V equipped with the spine fixation device will now be explained using FIGS. 7 and 8. FIGS. 7a-7c show the method of fixating a relative angle between the bone screw 1 and the retaining head 2. FIG. 8 shows the spine fixation device 100 attached to the vertebrae B of the spine V.

First, a tool is used to partially embed the bone screw 1 into the vertebra B of the spine V. Specifically, a tool is inserted into the tool receiving depression 13 and the bone screw 1 is rotated to screw the bone screw 1 into the vertebra B (see FIG. 8). Here, two bone screws 1 are installed in a direction along the X-axis in each of the two vertebrae B that are lined up in a direction along the Y-axis with a specified distance between each bone screw 1. In FIG. 8, only one bone screw 1 for each of the two vertebrae B is shown.

Next, the retaining bead 2 is attached to the bone screw 1. The legs 211b of the inner member 21 are spread outward in a direction along the X-axis and Y-axis, and the screw head 12 of the bone screw 1 is forced into the screw head receiving section 211. In this position, the bone screw 1 and the retaining head 2 are not fixed at an angle relative to one another. Another embodiment allows the joining of the bone screw 1 and the retaining head 2 to also be done before the bone screw 1 is installed into the vertebra B. In essence, the bone screw 1 can be installed into the vertebrae B of the spine V while the bone screw 1 and the retaining head 2 are joined together.

Figure 7A:
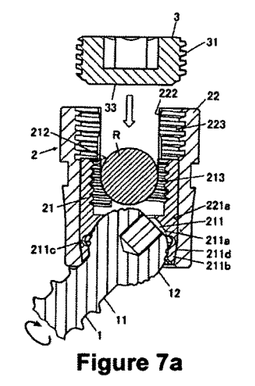
FIGS. 7a-7c are views showing a method of fixing the bone screw and the retaining head at a relative angle.
Figure 7B:
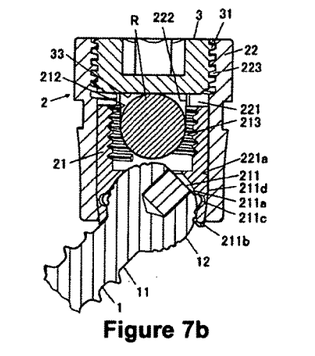
Figure 7C:
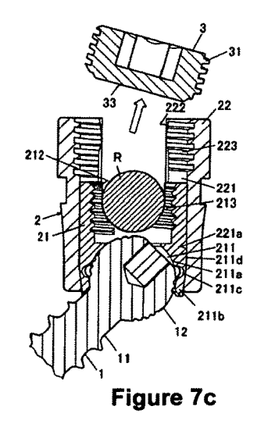
Figure 8:
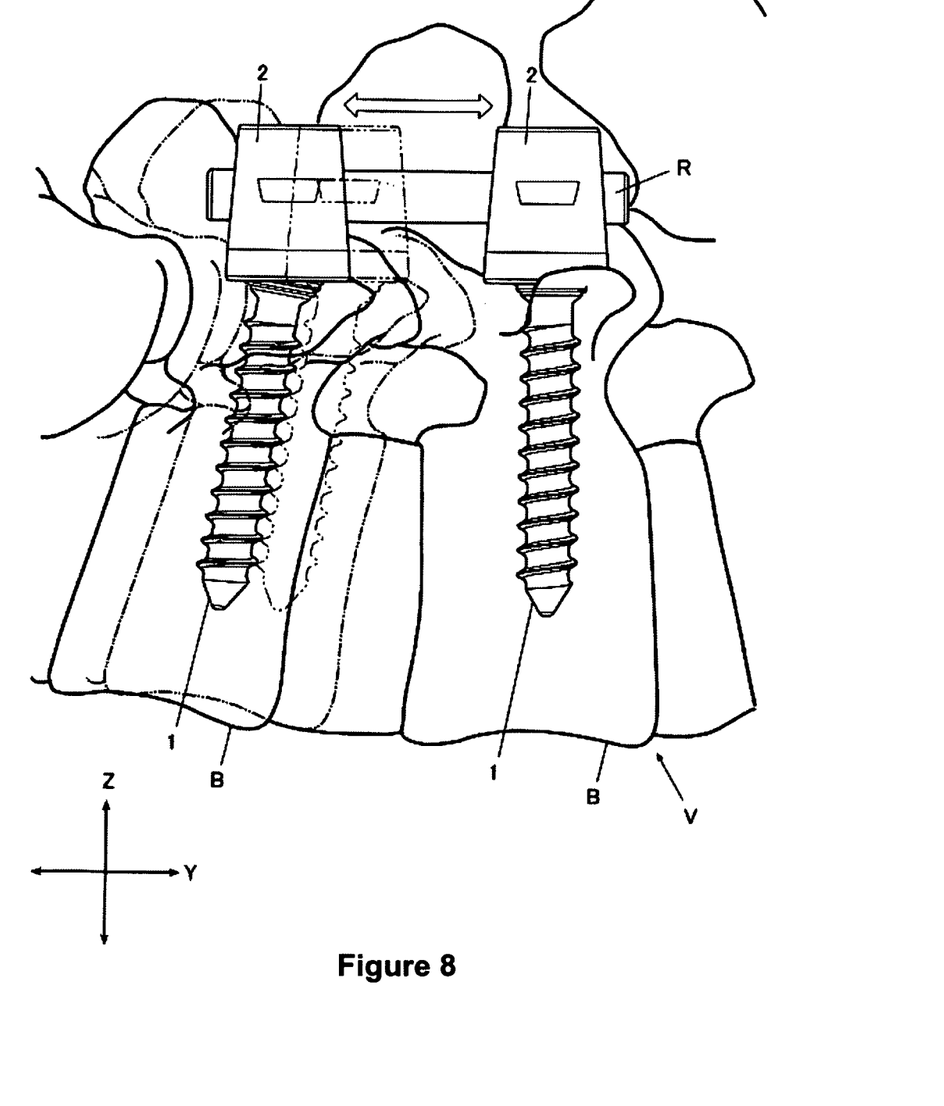
FIG. 8 is a view showing a method of using the spine fixation device when the relative angle between the bone screw and the retaining bead is fixed.

Continuing on, the rod R is placed in the inner rod receiving section 212 and an inner side of the outer rod receiving section 222 (see FIG. 7a). Specifically, the rod R is placed in the inner rod receiving section 212 and the inside of the outer rod receiving section 212 of each spine fixation device 100 aligned in a direction along the Y-axis.

Then, a specified torque is applied to the set screw 3 to screw the set screw 3 into the set screw receiving section 223. The planar part 33 of the set screw 3 comes into contact with the outer circumference of the rod R such that the rod R is sandwiched between the set screw 3 and the inner rod placement section 212 and moved toward the vertebrae B. Due to the sandwiching between the inner rod receiving section 212, the inner member 21 will move toward the vertebrae B in a direction along the Z-axis relative to the outer member 22. At this time, the legs 211b of the screw head receiving section 211 will be forced into a part of the inner arc of the storage part 221 of the outer member 22 that is smaller than the outer arc of the legs 211b. This causes the legs 211b of the screw head receiving section 211 to be squeezed due to the inner part 211a of the storage part 221. Due to the inner face of the screw head receiving section 211, the screw head 12 of the bone screw 1 will be forced toward the center direction. Then, when the outer circumference of the rod R comes into contact with an edge of the outer rod receiving section 222, the relative motion between the inner member 21 and the outer member 22 is stopped. In this condition, the bone screw 1 and the retaining head 2 are fixed at an angle relative to one another (see FIG. 7b).

As mentioned above, the screw head 12 of the bone screw 1 is pressured by the screw head receiving section 211. As such even if the set screw receiving section 223 and the set screw 3 threading is unlocked, it is possible to fix the bone screw 1 and the retaining head 2 at a relative angle (see FIG. 7c). Due to this, when moving one spine fixation device 100 relative to the other spine fixation device 100 in a direction along the y-axis to adjust the distance between the vertebra B, even if there is a large load on the bone screw 1 and/or the retaining head 2, the possibility of the angle of the bone screw 1 relative to the retaining head 2 changing is eliminated (see FIG. 8).

Hence, after adjusting the distance between the vertebrae B, the set screw 3 can be threaded back into the set screw receiving section 223 to fixate the spine fixation device 100 relative to the rod R in the desired position.

Next, the method of unlocking the angle of the bone screw 1 relative to the retaining head 2 will be explained using FIGS. 9 and 10.

Figure 9:
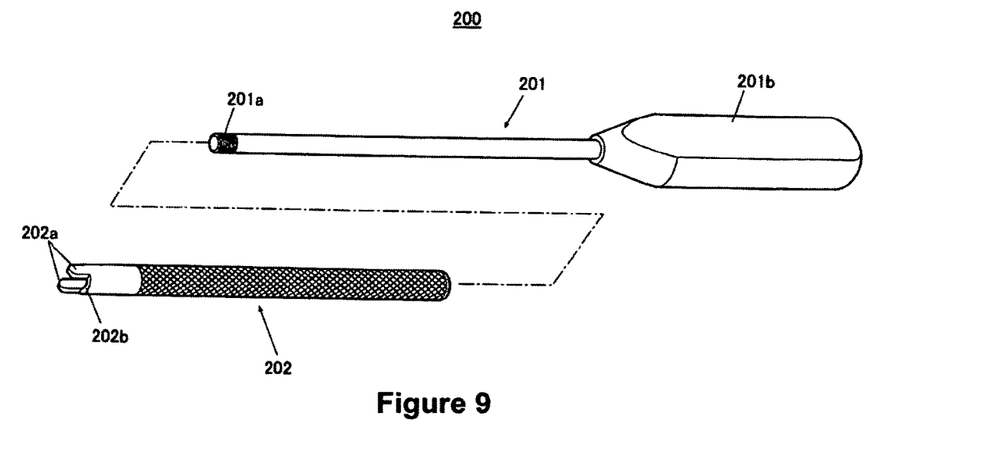
FIG. 9 is an isometric disassembled view of a unlocking device for use with the present invention.
Figure 10A:
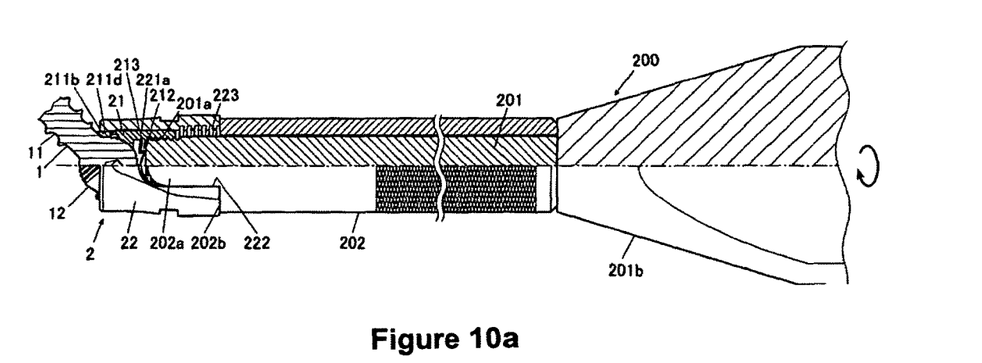
FIGS. 10a and 10b are partial cross sectional view showing how the unlocking device can be used to unlock the bone screw and the retaining head.
Figure 10B:
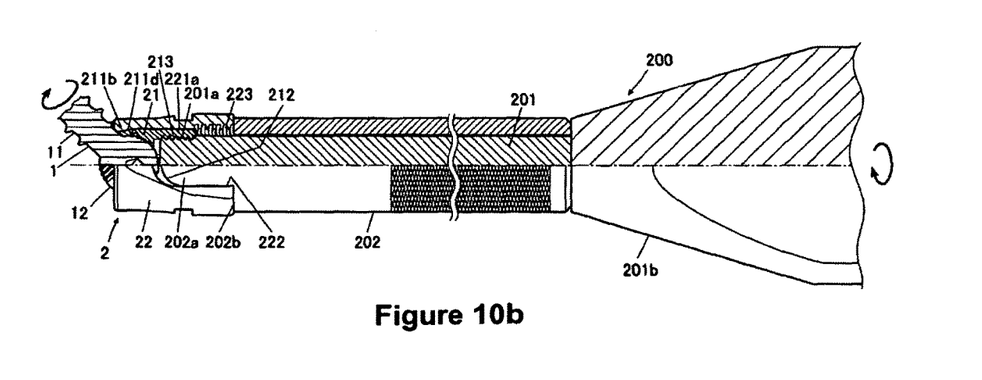

First, FIG. 9 will be used to explain the unlocking device 200. The unlocking device includes a tube shaped placement determining member or positioning member 202 that has a screw member 201.

The screw member 201 has a roughly cylindrical shape with a male screw part 201a constructed at one end and a handle 201b constructed at an opposite end. The male screw part 201a has a pitch and screw thread that makes it possible for the male screw pert 201a to thread into the unlocking female screw 213.

The placement determining member 202 contacts an edge of the outer member 22 and determines placement. Specifically, the placement determining member 202 is structured to be roughly the same length and shape as the length and shape of the screw member 201. One edge of the placement determining member 202 includes an engagement part 202a that protrudes into the cavity formed by the inner red receiving section 212. The edge of the placement determining member 202 further includes an abutting part 202b that engages an upper edge of the outer member 22.

The engagement part 202a is structured to be U-shaped in cross section. Specifically, by cutting out parts of the sidewall of the placement determining member 202 there are two U-shapes in the cross section of the engagement part 202a. The abutting part 202b is formed between the two U-shapes of the engagement part 202a.

The length of the engagement part 202a of the placement determining member 202, essentially the length from the abutting part 202b to the edge of the engagement part 202a, is shorter than the depth of the outer rod receiving section 222. Therefore, when the abetting part 202b abuts against an edge of the outer member 22, the frontal edge of the engagement part 202a is not in contact with an inner face of the outer rod receiving section 222 (see FIGS. 10a and 10b).

In addition, the side edge of the engagement part 202a is structured to have roughly the same curvature as the inner face of the inner rod receiving section 212 so that the engagement part 202a can come into contact with the inner face of the inner rod receiving section 212. Additionally, the engagement part 202a is thicker than the outer rod receiving section 222 in a direction orthogonal to the longitudinal axis of the engagement part 202a. Specifically, the engagement part 202a is as thick as or very slightly thicker than, the sum of the thicknesses of the outer rod receiving section 222 and the inner rod receiving section 212, so that the engagement part eventually engages the inner member 21.

The above mentioned unlocking device 200 and the spine fixation device 100 make up the spinal fixation system.

A fixation removal method will now be explained. In the fixation removal method explained below, the set screw 3 and rod R are removed from the retaining bead 2 of the spine fixation device 100 beforehand. In addition, the screw 201 is placed inside the placement determining member 202.

First, the placement determining member 202 is placed on the spine fixation device 100 such that the engagement part 202a is placed in the inside of the inner rod placement part 212 as well as the outer rod receiving section 222 thereby abutting the abutting part 202b against the edge of the outer member 22. Due to this, the position of the unlocking device 200 is determined with respect to the outer member 22 (see FIG. 10a).

Then, a user rotates the handle 201b relative to the placement determining member 202 to rotate the screw 201. The male screw part 201a of the screw 201 is screwed into the unlocking female screw 213. The screw 201 is rotated so that the handle 201b engages an axial end of the placement determining member 202 opposite from the engagement part 202a. The screw 201 is rotated further after the handle 201b engages the placement determining member 202. Due to this, the inner member 21 is pulled toward the unlocking device 200 since the screw 201 cannot move axially relative to the outer member 22. Essentially, the inner member 21 moves in a direction along the Z-axis relative to the outer member 22 away from the spine V, and the inner face 221a of the storage part 221 causes the arms 211b of the screw head receiving section 211 to loosen. As a result, the contact between the inner face 221a and the outer face 211d of the screw head receiving section 211 is freed, thereby removing the pressure on the screw head 12 of the bone screw 1 so that the angle of the bone screw 1 relative to the retaining head 2 is unlocked.

By having moved the inner member 21 upward, the a screw head receiving section 211 of the inner member and thereby the plurality of arms 211b of the inner member have enough space to deform outward to allow the retaining head 2 to be pulled off of the bone screw 1. This facilitates the removal of the retaining head 2 off of the bone screw 1.

As mentioned above, according to the practical form of the spine fixation device 100, the retaining head 2 includes the inner member 21 that has the screw head receiving section 211 where the screw head 12 of the bone screw 1 is placed and the outer member 22 that has the inner face 221a that can contact the outer face 211d of the screw head receiving section 211. As such, when the inner face 221a of the outer member 22 is in contact with the outer face 211d of the screw head receiving section 211, the screw head 12 of the bone screw 1 is pressured such that the angle of the bone screw 1 relative to the retaining head 2 is fixed. The parts that were needed to fixate the angle between the bone screw 1 and the retaining head 2 in previous technology (e.g., rings) becomes unnecessary. Thus, it becomes possible to fixate the relative angle between the bone screw 1 and the retaining head 2 using a much simpler structure. By having the screw head 12 of the bone screw 1 pressured by the screw head receiving section 211f it is possible to make the fixation of the relative angle of the bone screw 1 and the retaining bead 2 much stronger. As a result, not only can this reduce the number of parts and complexity of the spine fixation device 100, it is also possible to control the deterioration of operability and/or cost of the spine fixation device 100.

When the rod R is placed in the inner rod receiving section 212 of the inner member 21 and moved in a direction along the Z-axis, the inner member 21 moves relative to the outer member 22 such that the gradually reducing diameter of inner face 221a of the outer member 22 comes into contact with the outer face 211d of the screw head receiving section 211. With just the movement of the rod R in a direction along the Z-axis. It is possible to have the screw head 12 of the bone screw 1 pressured by the screw head receiving section 211. Specifically, by having the inner member 21 move relative to the outer member 22, the spaces between the arms 211b are narrowed and the screw head receiving section 211 is fastened by the inner face 221a of the outer member 22 such that the screw head 12 of the bone screw 1 is pressured by the inner face of the screw head receiving section 211. At this time, by having the set screw 3 screw into the set screw receiving section 223 of the outer member 22, the front edge of set screw 3 moves the rod R in a direction along the Z-axis. By using the set screw 3 to move the rod R, it is possible to have the screw head 12 of the bone screw 1 be pressured by the inner face of the screw head receiving section 211 in a much simpler structure. Moreover, in such a state, it is possible to remove the set screw 3 from the set screw receiving section 223 and still maintain the fixation of the angle of the bone screw 1 relative to the retaining head 2.

When the bone screw 1 is not fixated relative to the retaining head 2, it is possible to embed the bone screw 1 into the vertebra B much more easily since the screw head 12 is structured to be easily attached and detached from the screw head receiving section 211. Essentially, after embedding the bone screw 1, it is possible to install the screw head 12 into the screw head receiving section 211. Alternatively, it is possible to embed the bone screw 1 with the screw head 12 already installed into the screw head receiving section 211.

By having the unlocking device 200 include the placement determining member 202 and the screw 201. It is possible to free the fixated relative angle between the bone screw 1 and the retaining head 2 in a much easier way. Essentially, when the relative angle between the bone screw 1 and the retaining head 2 is fixated, the placement determining member 202 can hold the position of the unlocking device 200 relative to the outer member 22, and the screw 201 can be screwed into the unlocking female screw 213 of the inner member 21. The inner member 21 can then be moved relative to the outer member 22 in a direction along the Z-axis to release the contact between the inner face 221a of the outer member 22 and the screw head receiving section 211. Due to this, the pressure of the screw head placement part 211 on the screw head 12 of the bone screw is released, and the fixated relative angle between the bone screw 1 and the retaining head 2 can be released. As such, after the relative angle between the bone screw 1 and the retaining head 2 has been fixated, the unlocking device 200 can be used to release the fixated relative angle between the bone screw 1 and the retaining head 2 to allow for readjustment of the angle in a much easier way.

The invention is not limited to just the aforementioned specifically discussed examples, and changes in the design of the invention are allowed within the gist of the invention so long as the changes do not deviate from the inventions parameters. For example, in the aforementioned specifically discussed example, the rod R is moved in a direction along the Z-axis by the set screw 3 so that the inner face 221a of the outer member 22 comes into contact with the outer face 211d of the screw head receiving section 211. However, this is just one example and the invention is not limited to only this way. Any other appropriate design options can be used so long as the design is structured such that the screw head 12 of the bone screw 1 is pressured by the screw head receiving section 211.

Again, in the aforementioned specifically discussed example, the unlocking device 200 includes the placement determining member 202 and the screw 201. The structure of the unlocking device 200 is just one example and is not limited to just the specific example. For example, the unlocking device 200 can have a mechanism that prevents the screw 201 from slipping out relative to the placement determining member 202.

Furthermore, in the aforementioned specifically discussed example, the rod R is roughly cylindrical, however other shapes can be used, if the shape of the rod R is something other than a cylinder, the inner rod receiving section 212 and the outer rod receiving section 222 can be structured according to the shape of the outer face of the rod R.

Additionally, in the specifically discussed examples presented, it should be noted that all design details are suggestion and not limiting factors. The parameters of the present invention are not limited by the aforementioned explanation, but by the patent claims. The present invention is intended to have the parameters of the patent claims and design changes within the parameters.

What is claimed is:

1. A spine fixation system comprising:
a rod for fixating a spine;
an elongated bone screw configured to be partially embedded in a vertebra of the spine;
a retaining head holding the rod and the bone screw, the retaining head including an inner member having a head receiving section for receiving a screw head of the elongated bone screw and an outer member surrounding the inner member, the inner member having an outer face that contacts an inner face of the outer member;
wherein contact between the outer face and the inner face results in pressure being applied to the screw head to fix the elongated bone screw at an angle relative to the retaining head; and
an unlocking device that removes the pressure being applied to the screw head to fix the elongated bone screw at an angle relative to the retaining head, the unlocking device directly engaging the inner member and directly engaging the outer member to axially move the inner member relative to the outer member to remove the pressure being applied to the screw head, the unlocking device having a positioning member and a screw movable relative to each other, the positioning member including at least one engagement part protruding from an edge of the positioning member, the at least one engagement part extending into a cavity in the inner member, the positioning member directly engaging the outer member to position the unlocking device relative to the outer member and the screw threadably engaging a female screw provided on the inner member, the screw rotating relative to the inner member, the outer member and the positioning member to axially move the inner member relative to the outer member.

2. The spine fixation system of claim 1, wherein the inner face and the outer face gradually decrease in diameter along a Z-axis, and wherein the inner member moves along the Z-axis to put the inner face in contact with the outer face.

3. The spine fixation system of claim 2, wherein the inner member is divided in the circumferential direction about the Z-axis into parts, the inner member moving along the Z-axis such that the inner face squeezes the inner member to cause the parts of the retaining head to narrow such that pressure is applied the screw head.

4. The spine fixation system of claim 3, wherein the inner member has a rod receiving section for receiving the rod, and wherein the rod is moved along the Z-axis to cause movement of the inner member along the Z-axis to put the inner face in contact with the outer face.

5. The spine fixation system of claim 4, wherein the outer member has a set screw receiving section for receiving a set screw, the set screw being rotated to fixate the rod in the rod receiving section, the set screw being configured to apply pressure to the rod in a direction along the Z-axis.

6. The spine fixation system of claim 5, wherein the relative angle between the elongated bone screw and the retaining head can be maintained when the set screw is removed.

7. The spine fixation system of claim 6, wherein the screw head can be detached from the retaining head when the bone screw is not fixed at an angle relative to the retaining head.

8. The spine fixation system of claim 1, wherein the screw is prevented from moving axially relative to the outer member and thereby the screw moves the inner member axially relative to the outer member.

9. The spine fixation system of claim 1, wherein the at least one engagement part is U-shaped.

10. The spine fixation system of claim 1, wherein the positioning member includes an abutting part that engages an upper edge of the outer member.

11. The spine fixation system of claim 1, wherein the at least one engagement part includes two engagement parts and the abutting part is between the two engagement parts.

* * * * *